(12) United States Patent
Mullins

(10) Patent No.: US 6,235,305 B1
(45) Date of Patent: May 22, 2001

(54) ESSENTIALLY NONABSORBABLE LIPASE INHIBITOR DERIVATIVES, PHARMACEUTICAL COMPOSITIONS AND METHODS OF USE THEREFOR

(75) Inventor: John Jason Gentry Mullins, San Francisco, CA (US)

(73) Assignee: 2Pro Chemical, Dover, DE (US)

( * ) Notice: Subject to any disclaimer, the term of this patent is extended or adjusted under 35 U.S.C. 154(b) by 0 days.

(21) Appl. No.: 09/431,551

(22) Filed: Oct. 29, 1999

(51) Int. Cl.$^7$ .................................................... A61K 47/00
(52) U.S. Cl. .............................. 424/439; 514/54; 514/55; 514/57; 514/59
(58) Field of Search .................................. 514/54, 55, 57, 514/59, 909, 675; 424/439

(56) References Cited

U.S. PATENT DOCUMENTS

| | | | | |
|---|---|---|---|---|
| 5,540,917 | * | 7/1996 | Isler et al. | 424/78.01 |
| 5,616,570 | * | 4/1997 | Lange, III et al. | 514/54 |
| 5,643,874 | * | 7/1997 | Bremer et al. | 514/12 |
| 6,030,953 | * | 2/2000 | Bailly et al. | 514/25 |

* cited by examiner

Primary Examiner—Gollamudi S. Kishore
Assistant Examiner—Liliana Di Nola-Baron
(74) Attorney, Agent, or Firm—Robert Lev

(57) ABSTRACT

This invention provides lipase inhibitors that have been rendered non-absorbable by linking such lipase inhibitors to a non-absorbable support, pharmaceutical comprising such lipase inhibitors and method of use therefor to treat adiposity or obesity.

5 Claims, No Drawings

ESSENTIALLY NONABSORBABLE LIPASE INHIBITOR DERIVATIVES, PHARMACEUTICAL COMPOSITIONS AND METHODS OF USE THEREFOR

FIELD OF THE INVENTION

This invention relates to lipase inhibitors that have been rendered non-absorbable by linking such lipase inhibitors to a non-absorbable support.

BACKGROUND OF THE INVENTION

Lipase inhibitors such as esterastin (see U.S. Pat. No. 4,189,438), tetrahydroesterastin (3,5-hydroxy-2hexadeca-7, 10-dienoic 1,3-lactone), 3,5-dihydroxy-2-hexylhexadeca-7, 10-dienoic 1,3-lactone, 3,5-di-hydroxy-2-hexylhexadecanoic 1,3-lactone, and the like, are well-known as lipase inhibitors and as pancreatic cholesterol esterase inhibitors. However, such lipase inhibitors are, inter alia, also substantially orally active as immunosuppressants (see U.S. Pat. No. 4,189,438 and U.S. Pat. No. 4,202,824), which can be a highly undesired side activity in a normal or immunosuppressed person.

A popular lipase inhibiting compound which is substantially non-absorbable is known as Orlistat ((2S,3S,5S)-5-[(S)-2-formamido4-methylvaleryloxy]-2-hexyl-3-hydroxy-hexadecanoic 1,3 acid lactone, see U.S. Pat. No. 5,643,874). Orlistat has been used to inhibit lipases in the body and thereby prevent the absorption of dietary fat. At a 120 mg dose of Orlistat, taken before consuming a fat-containing meal (or up to one hour after eating such a meal), up to one-third of the fat eaten at a given meal will not be absorbed by the average person and utilized as dietary fat calories. The undigested fat passes directly through the digestive system as an oil and is ehininated from the bowel in its oily undigested form.

Certain polysaccharides are non-absorbable and some polysaccharides have the side benefit of reducing lipid absorption by the body. Defatted rice germ polysaccharides and sulfated polysaccharides are also lipase inhibitors. The super fiber Chitosan, which is a deacylated polysaccharide derived from shellfish chitan, has an ability to absorb fat and cholesterol, particularly in combination with vitamin C. Chitosan compositions may actually absorb up to 6 to 8 times its weight in fat and oils. While the polysaccharide from shellfish is similar to crude cellulose plant fiber, it has the ability to significantly bind fat in the digestive system as compared to plant fiber. Further, since polysaccharides, including those which do not preferentially bind oils over water, are not absorbed by the digestive systems of anmals such as humans, non-human primates, dogs and cats, there is no caloric value to such polysaccharides and they pass through the such digestive systems unabsorbed and substantially intact. Examples of non-absorbable polysaccharides are polysaccharides having a molecular weight of greater than 8 kDa such as dextrans, molecular microcrystalline cellulose, wheat bran, oat bran, defatted rice germ, alginic acid, pectin, amylopectin, chitin, crude cellulose, argar, chitosan and the like.

There is a need in the art for non-absorbable lipase inhibitors, as well as for improved antiadiposity compositions and methods which do not require an absolute low-fat diet in order to lower the absorption of dietary fat as calories.

SUMMARY OF THE INVENTION

In one aspect the present invention relates to novel derivatives of lipase inhibitors which are non-absorbable. In particular, absorbable lipases such as esterastin are coupled to a non-absorbable biocompatible, pharmaceutically acceptable polymer support, such as a polysaccharide, to render the lipase essentially non-absorbable by the digestive system of an animal such as a dog, cat, non-human primate or humans. Preferred lipase inhibitors are at one lipase inhibitor which is a member selected from the group consisting of esterastin, tetrahydro-esterastin (3,5-hydroxy-2-hexadeca-7,10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like, wherein such lipase inhibitor is coupled to a non-absorbable biocompatible, pharmaceutically acceptable polymer support, such as a polysaccharide, to render the lipase non-absorbable by the digestive system of an animal such as a dog, cat, non-human primate or humans. Particularly preferred polysaccharides have at least one member selected from the group consisting of dextrans, molecular microcrystalline cellulose, wheat bran, oat bran, defatted rice germ, alginic acid, pectin, amylopectin, chitin, crude cellulose, argar, chitosan and the like. Particularly preferred bound lipase inhibitors are lipase inhibitors bound via a derivatized group on the lipase such as a derivatized nitrogen, acid or alcohol group to a group on the polymer support such as a derivatized alcohol, acid or amino group. Preferably, a diether bridge is formed between the lipase inhibitor and the support, wherein the bridge is derived from an alcohol group on the lipase and an alcohol group on the support, each reacting with an etherizing bridging group.

In another aspect the present invention relates to pharmaceutical compositions comprising a lipase inhibiting effective amount of at least one lipase inhibitor which is coupled to a digestively non-absorbable support. Preferred are such pharmaceutical compositions comprising an effective amount of a lipases coupled to a non-absorbable biocompatible, pharmaceutically acceptable polymer support, such as a polysaccharide, wherein the lipase is essentially non-absorbable by the digestive system of an animal such as a dog, cat, non-human primate or humans.

In still another aspect, the present invention relates to a method for treating adiposity or obesity by administering to a patient before a fat-contain meal, or up to one hour after such a meal is consumed, an amount of at least one lipase inhibitor which is bound to a non-absorbable polymer support in an amount effective to inhibit the absorption of up to one-third of the dietary fat in such a meal. In particular, a preferred method comprises administering at one lipase inhibitor which is a member selected from the group consisting of esterastin, tetrahydro-esterastin (3,5-hydroxy-2hexadeca-7,10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like, wherein such lipase inhibitor is coupled to a non-absorbable biocompatible, pharmaceutically acceptable polymer support, such as a polysaccharide, to render the lipase non-absorbable by the digestive system of an animal such as a dog, cat, non-human primate or humans. Particularly preferred polysaccharides are at least one member selected from the group consisting of dextrans, molecular microcrystalline cellulose, wheat bran, oat bran, defatted rice germ, alginic acid, pectin, amylopectin, chitin, crude cellulose, argar, chitosan and the like. Particularly preferred bound lipase inhibitors are lipase inhibitors bound via a derivatized nitrogen, acid or alcohol group to a derivatized alcohol, acid or amino group on the polymer support. A diether bridge between the lipase inhibitor and the support which is derived from an alcohol group on the lipase and an alcohol group on the support, respectively reacting with a bridging group is the preferred coupling of the lipase inhibitor to the support.

The preferred compounds also include their pharmaceutically acceptable isomers, hydrates, solvates, salts and pro-drug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

The term "bridging group" refers to a bifunctional chain or spacer group capable of reacting with one or more functional groups on a lipase inhibitor compound and then react with a second same or different functional group on a polymer compound in order to form a linked structure or conjugate between the two compounds. The bond formed between the bridging group and each of the two compounds must be of a type that is resistant to cleavage by the digestive environment. On one aspect, the bridging group is of the formula X—R—X, wherein R is a member selected from a straight-chained or branched alkyl group, a straight-chained or branched alkenyl group, a straight-chained or branched alkynyl group, a mono acyl group, a diacyl group and the like, and X is a functionally reactive group such as a halogen, under special reaction conditions as described hereinafter. Particularly preferred bridging groups form a diether or diacyl bridge that is resistant to cleavage by the digestive environment. Examples of alkylene dichloride bridging group forming compounds are dichloromethane, 1,2-dichloroethane, 1,2- and 1,3-dichloropropane, 1,2-, 1,3- and 1,4-dichlorobutane, and the like. Examples of acyldichloride bridging group forming compounds are oxalic acid dichloride, malonic acid dichloride, succinic acid dichloride, glutaric acid dichloride, adipic acid dichloride, pimelic acid dichloride, suberic acid dichloride, fumaric acid dichloride, malic acid dichloride, glutamic acid dichloride, terephthalic acid dichloride, isophthalic acid dichloride, and the like. Other such bridging group reagents are compounds such as epichlorhydrin, phosphorus oxychloride, and diphosphoryl tetrachloride, and the like.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fuilly saturated. Examples of such carbocyclic ring structures include, but are not limited to, cyclopropyl, cyclobutyl, cyclopentyl, cyclohexyl adamantyl cyclooctyl, [3.3.0]bicyclooctane, [4.3.0] bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring stucture having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or flly saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement (s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofiranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofin, furanyl, furazanyl, imidazolidinyl, imidazolinyl imidazolyl, 1H-indazolyl, indolinyl, indolizinyl, indolyl, 3H-indolyl, isobenzofuiranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofliranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fuised to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, suliric acid, nitric acid, phosphoric acid and the like, and organic acids such as acetic acid, propionic acid, glycolic acid, pyruvic acid, oxalic acid, maleic acid, malonic acid, succinic acid, filmaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

PREFERRED EMBODIMENTS

In one aspect the present invention relates to novel derivatives of lipase inhibitors which are non-absorbable. In particular, absorbable lipases such as esterastin are coupled to a non-absorbable biocompatable, pharmaceutically acceptable polymer support, such as a polysaccharide, to render the lipase essentially non-absorbable by the digestive system of an animal such as a dog, cat, non-human primate or hunans. Preferred lipase inhibitors are at one lipase inhibitor which is a member selected from the group consisting of esterastin, tetrahydro-esterastin (3,5-hydroxy-2-hexadeca-7,10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like, wherein such lipase inhibitor is coupled to a non-absorbable biocompatable, pharmaceutically acceptable polymer support, such as a polysaccharide, to render the lipase non-absorbable by the digestive system of an animal such as a dog, cat, non-human primate or humans. Particularly preferred polysaccharides have at least one member selected from the group consisting of dextrans, molecular microcrystalline cellulose, wheat bran, oat bran, defatted rice germ, alginic acid, pectin, amylopectin, chitin, crude cellulose, argar, chitosan and the like. Particularly preferred bound lipase inhibitors are lipase inhibitors bound via a at least one ether bond (from condensing two hydroxyl groups) or via a derivatized group on the lipase such as a derivatized nitrogen, acid or alcohol group to a group on the polymer support such as a derivatized alcohol, acid or amino group. Preferably, at least one and or two ether bridges are formed between the lipase inhibitor and the support, wherein the bridge is derived from an alcohol group on the lipase and an alcohol group on the support, each reacting with one another or with an etherizing bridging group.

Lipase inhibitors having a free hydroxy group such as tetrahydro-esterastin (3,5-hydroxy-2-hexadeca-7,10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like, are easily coupled to a polymer support having free hydroxy groups such as cellulose, chitosan and other polysaccharides having free hydroxyl groups. The lipase inhibitor molecule is condensed to form an ether linkage as shown in polysaccharide chemistry or is reacted with a dihalide bridging group, such as an alkylene dihalide, in a molar ratio of 1:1 to etherize one of the free hydroxyl groups on the lipase inhibitor or replace a hydrogen atom an an amino group. If necessary, the resulting linked or monoether lipase inhibitor intermediate compound is then reacted with a polymer support compound having a free hydroxyl group to form an alkylene diether bridge between the lipase inhibitor and the polymer support. Particularly preferred polymer supports are polysaccharides having multiple free hydroxyl group which after coupling may optionally be sulfonated to render the lipase support itself a lipase inhibitor compound. Etherification procedures are well-known in the art and well within the routine skill of the ordinary practitioner. Further, other bridging groups and the techniques for binding a compound having a reactive functional group to a polymer support are well-known in the art. The preferred compounds also include their pharmaceutically acceptable isomers, hydrates, solvates, salts and prodrug derivatives.

The bridging group refers to a bifunctional chain or spacer group capable of reacting with one or more functional groups on a lipase inhibitor compound and then react with a second same or different functional group on a polymer compound in order to form a lied structure or conjugate between the two compounds. The bond formed between the bridging group and each of the two compounds must be of a type that is resistant to cleavage by the digestive environment. On one aspect, the bridging group is of the formula X—R—X, wherein R is a member selected from a straight-chained or branched alkyl group, a straight-chained or branched alkenyl group, a straight-chained or branched alkynyl group, a mono acyl group, a diacyl group and the like, and X is a functionally reactive group such as a halogen, under special reaction conditions as described hereinafter. Particularly preferred bridging groups form a diether or diacyl bridge that is resistant to cleavage by the digestive environment.

Examples of alkylene dichloride bridging group forming compounds are dichloromethane, 1,2-dichloroethane, 1,2- and 1,3-dichloropropane, 1,2-, 1,3- and 1,4-dichlorobutane, and the like. Examples of acyldichloride bridging group forming compounds are oxalic acid dichloride, malonic acid dichloride, succinic acid dichloride, glutaric acid dichloride, adipic acid dichloride, pimelic acid dichloride, suberic acid dichloride, flimaric acid dichloride, malic acid dichloride, glutamic acid dichloride, terephthalic acid dichloride, and isophthalic acid dichloride, and the like. Other such bridging group reagents are compounds such as epichlorhydrin, phosphorus oxychloride, and diphosphoryl tetrachloride, and the like.

The preferred halogen is a chlorine group. The reaction is performed by the slow addition of a bifunctional reagent such as an diacyl dichloride or alkylene dichloride, dissolved in a substantially water immiscible organic solvent, to an alkaline aqueous solution of the lipase inhibitor in a substantially 1:1 molecular ratio. The reaction proceeds at the interface between the two immiscible solutions to provide an interfacial condensation and produce the sucrose derivative or analogue. It has been discovered that this reaction at the interface of the organic solution and the aqueous solution imparts a specificity to the reaction for primary alcohol groups of the polysaccharide. It should be understood that equivalent reactants such as diepoxides and halohydrocarbyloxiranes such as epichlorohydrin also react in the process to provide new and useful ether bridges.

By appropriate selection of the type of bridging group reactant, different structural groups with various chemical properties can be incorporated into the resulting bridge and various types of lipase inhibitors can be connected to a nonabsorbable polymer support, such as a polysaccharide, and preferably to chitosan. Reaction temperatures and other reactions conditions, as well are reactant proportions are well within the skill of the ordinary polymer chemist practitioner. Other groups and modifications will be apparent to one of ordinary skill in the art from the above discussion.

The lipase inhibitor functionality of the coupled lipase inhibitors may be determined by well-known lipase inhibitor assays. A therapeutically effective amount of the bound lipase inhibitor may be administered to a patient. Additional fat binding polymers may optionally be added to the composition.

In one aspect, the present invention provides a sports drink, snack, nutrient supplement, food or power which may be formulated to contain a lipase inhibiting therapeutically effective amount of the lipase inhibitor composition according to the invention.

In another aspect the present invention relates to pharmaceutical compositions comprising a lipase inhibiting effective amount of at least one lipase inhibitor which is coupled to a digestively non-absorbable support. Preferred are such pharmaceutical compositions comprising an effective amount of a lipases coupled to a non-absorbable biocompatable, pharmaceutically acceptable polymer support, such as a polysaccharide, wherein the lipase is essentially non-absorbable by the digestive system of an animal such as a dog, cat, non-human primate or humans. The pharmaceutical composition can be administered to a patent prior to or within one hour of consuming a fat-containing meal to prevent absorption of up to one-third of the dietary fat consumed at the meal.

In still another aspect, the present invention relates to a method for treating adiposity or obesity by administering to a patient before a fat-contain meal, or up to one hour after such a meal is consumed, an amount of at least one lipase inhibitor which is bound to a non-absorbable polymer support in an amount effective to inhibit the absorption of up to one-third of the dietary fat in such a meal . In particular, a preferred method comprises administering at one lipase inhibitor which is a member selected from the group consisting of esterastin, tetrahydro-esterastin (3,5-hydroxy-2 hexadeca-7,10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like, wherein such lipase inhibitor is coupled to a non-absorbable biocompatable, pharmaceutically acceptable polymer support, such as a polysaccharide, to render the lipase non-absorbable by the digestive system of an animal such as a dog, cat, non-human primate or humans. Particularly preferred polysaccharides are at least one member selected from the group consisting of dextrans, molecular microcrystalline cellulose, wheat bran, oat bran, defatted rice genii, alginic acid, pectin, amylopectin, chitin, crude cellulose, argar, chitosan and the like. Particularly preferred bound lipase inhibitors are lipase inhibitors bound via a derivatized nitrogen, acid or alcohol group to a derivatized alcohol, acid or amino group on the polymer support. A diether bridge between the lipase inhibitor and the support which is derived from an alcohol group on the lipase and an alcohol group on the support, respectively reacting with a bridging group is the preferred coupling of the lipase inhibitor to the support.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are usefuil for the preparation of the salts described above and are known to those skilled in the art. For example, the free acid or free base form of a compound of one of the above compounds can be reacted with one or more molar equivalents of the desired acid or base in a solvent or solvent mixture in which the salt is insoluble, or in a solvent like water after which the solvent is removed by evaporation, distillation or freeze drying.

Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of fluctionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serun albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. Accordingly, it may be necessary for the therapist to titer the dosage and modify the means of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion. A preferred dosage is an amount that has a similar lipase inhibiting effect to the lipase inhibition of 120 mg of orally taken orlistat. The determination of such equivalent lipase inhibition can be determined via well-known lipase inhibition assays, and may be either an in vivo assay, an in vitro assay, or both.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

The lipase inhibitor compounds, polymer supports and bridging groups of the present invention may be synthesized or readily obtained from commercially available sources. Polymer bridging groups, bridge coupling processes and compound purification methods are described and referenced in standard textbooks, particularly the coupling of alcohol groups via diether bridges. Standard polymer textbooks reference typical bifunctional bridging groups and coupling procedures.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the fmlctional groups may be protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are usefuil for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by oral tablet, capsule, etc., other methods of administration are also anticipated such as in sports drinks, reconstitutable powders or foodstuffs employing a variety of dosage forms are contemplated.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. The lipase inhibition efficiency must be individually determined for each inhibitor by methods well known in pharmacology. Accordingly, it may be necessary for the therapist to titer the dosage and modify the type of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, either prior to a fat-containing meal or within one hour after such a meal, but other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, and the like. Other materials of various types may be used as coatings or as modifiers of the physical form of the dosage unit. Sterile compositions for drinking can be formulated according to conventional pharmaceutical practice. For example, dissolution or suspension of the active compound in a liquid vehicle. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as antilipase, anticholesterolemic agents, and other dietary agents, such as an appetite suppressant and the like. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit lipid absorption in the body and reduce the availability of dietary fat as dietary calories.

The compounds of this present invention, selected and used as disclosed herein, are believed to be useful for preventing or treating a condition characterized by undesired adiposity. In addition to the treatment of obesity, the compositions or active substance combination, in accordance with the invention, can be used for the treatment and prevention of overweight, such as diabetes, hypertension, hyperlipidemia and insulin-resistance syndrome.

In the case of all of these indications, the active substances can be used in the dosage ranges given above, with the individual dosage depending on the nature of the illness to be treated as well as on the age and condition of the patient and can be determined within the purview of the medical specialist.

Without further description, it is believed that one of ordinary skill in the art can, using the preceding description, make and utilize the compositions of the present invention and practice the claimed methods. The examples of lipase inhibitors and lipophilic polysaccharides as well as their therapeutic proportions, specifically point out preferred embodiments of the present invention, and are not to be construed as limiting in any way the remainder of the disclosure. Such examples are non-limiting in that one of ordinary skill (in view of the above) will readily envision other permutations and variations on the invention without departing from the principal concepts. Such permutations and variations are also within the scope of the present invention.

What is claimed is:

1. A composition comprising a compound having at least one lipase inhibitor moiety which is bound to a non-absorbable biocompatible, pharmaceutically acceptable polysaccharide polymer support by at least one chemical bond which is substantially non-clevable by the digestive system of a dog, cat, non-human primate or a human, whereby the lipase inhibitor is essentially non-absorbable, wherein:

(a) the lipase inhibitor moiety is bound via a derivatized nitrogen, acid or alcohol group to a divalent bridging group, which is in turn bound to the polymer support by a derivatized alcohol, acid or amino group on the polymer support;

(b) the divalent bridging group is a member selected from the group consisting of a straight or branched chain alkylene bridging group, an alkenyl bridging group, an alkynyl bridging group, a monoacyl group, and a diacyl group; and (c) the lipase inhibitor moiety is a member selected from the group consisting of orlistat, esterastin, 3,5-hydroxy-2-hexadeca-7,10-dienoic 1,3-lactone, 3,5-dihydroxy-2-hexylhexadeca-7,10-dienoic 1,3-lactone, and 3,5-di-hydroxy-2-hexylhexadecanoic 1,3-lactone.

2. A composition comprising a compound having at least one lipase inhibitor moiety which is bound to a non-absorbable biocompatible, pharmaceutically acceptable polysaccharide polymer support, which support is a member selected from the group consisting of: a dextran, microcrystalline cellulose, wheat bran, oat bran, defatted rice germ, alginic acid, pectin, amylopectin, chitin, crude cellulose, argar and chitosan, by at least one chemical bond which is substantially non-clevable by the digestive system of a dog, cat, non-human primate or a human, whereby the lipase is essentially non-absorbable;

wherein:
- (a) the lipase inhibitor moiety is bound via a derivatized nitrogen, acid or alcohol group to a divalent bridging group, which is in turn bound to the polymer support by a derivatized alcohol, acid or amino group on the polymer support;
- (b) the divalent bridging group is a member selected from the group consisting of a straight or branched chain alkylene bridging group, an alkenyl bridging group, an alkynyl bridging group, a monoacyl group, and a diacyl group: and,
- (c) the lipase inhibitor moiety is a member selected from the group consisting of orlistat, esterastin, 3,5-hydroxy-2-hexadeca-7,10-dienoic 1,3-lactone 3,5-dihydroxy-2-hexylhexadeca-7,10-dienoic 1,3-lactone, and 3,5-di-hydroxy-2-hexylhexadecanoic 1,3-lactone.

3. A pharmaceutical composition comprising a therapeutically effective amount of at least one composition according to claim 1 and a pharmaceutically acceptable carrier or diluent.

4. A foodstuff composition comprising a lipase inhibiting effective amount of at least one composition according to claim 1.

5. A method of treating adiposity comprising treating a dog, cat, non-human primate or a human with a lipase iiibiting effective amount of at least one composition according to claim 1.

* * * * *